(12) United States Patent
Asami et al.

(10) Patent No.: US 10,156,500 B2
(45) Date of Patent: Dec. 18, 2018

(54) EXHAUST GAS DILUTION DEVICE

(71) Applicant: HORIBA, Ltd., Kyoto (JP)

(72) Inventors: Tetsuji Asami, Kyoto (JP); Yoshitomo Takakura, Kyoto (JP)

(73) Assignee: Horiba, Ltd., Kyoto (JP)

( * ) Notice: Subject to any disclaimer, the term of this patent is extended or adjusted under 35 U.S.C. 154(b) by 120 days.

(21) Appl. No.: 14/404,840

(22) PCT Filed: Apr. 17, 2013

(86) PCT No.: PCT/JP2013/061398
§ 371 (c)(1),
(2) Date: Dec. 1, 2014

(87) PCT Pub. No.: WO2013/179794
PCT Pub. Date: May 12, 2013

(65) Prior Publication Data
US 2015/0153255 A1 Jun. 4, 2015

(30) Foreign Application Priority Data

Jun. 1, 2012 (JP) ................................ 2012-126046

(51) Int. Cl.
*G01N 1/22* (2006.01)
*G01N 33/00* (2006.01)
*G01M 15/10* (2006.01)

(52) U.S. Cl.
CPC ........ *G01N 1/2252* (2013.01); *G01M 15/102* (2013.01); *G01N 33/0018* (2013.01); *G01N 33/0022* (2013.01); *G01N 2001/2255* (2013.01)

(58) Field of Classification Search
CPC ............... G01N 1/2247; G01N 1/2252; G01N 2001/2264
USPC .................................. 73/23.31, 23.33, 28.01
See application file for complete search history.

(56) References Cited

U.S. PATENT DOCUMENTS

| 4,586,367 A | 5/1986 | Lewis |
| 6,151,952 A | 11/2000 | Mathews et al. |
| 2008/0190168 A1* | 8/2008 | Booker ................ G01N 1/2202 73/1.25 |
| 2011/0048105 A1* | 3/2011 | Graze, Jr. ............ G01N 1/2202 73/23.31 |

(Continued)

FOREIGN PATENT DOCUMENTS

| CN | 102589959 A | 7/2012 |
| EP | 1285267 A | 11/2001 |

(Continued)

OTHER PUBLICATIONS

Office Action dated Feb. 22, 2016 issued for Chinese patent application No. 201380028860.X, 12 pgs.

(Continued)

*Primary Examiner* — David M Gray
*Assistant Examiner* — Andrew V Do
(74) *Attorney, Agent, or Firm* — Brooks Kushman P.C.

(57) ABSTRACT

The present invention is intended that diluted exhaust gas is supplied to a plurality of measurement instruments by a single exhaust gas dilution device to thereby reduce in size an exhaust gas measurement system incorporated with the exhaust gas dilution device and dilute exhaust gas with the same exhaust gas under the same dilution condition in the plurality of measurement instruments.

7 Claims, 4 Drawing Sheets

(56) References Cited

U.S. PATENT DOCUMENTS

2012/0174989 A1  7/2012  Otsuki et al.

FOREIGN PATENT DOCUMENTS

| JP | 62-010639 U | 1/1987 |
| JP | 63-038036 U | 3/1988 |
| JP | 02-213739 | 8/1990 |
| JP | 07-005044 U | 1/1995 |
| JP | 08-226879 | 9/1996 |
| JP | 10-123029 | 5/1998 |
| JP | 11-326161 | 11/1999 |
| JP | 2000-338015 | 12/2000 |
| JP | 2001-165827 | 6/2001 |
| JP | 2005062056 A | 3/2005 |
| JP | 2006-153716 A | 6/2006 |
| JP | 2006-153746 | 6/2006 |
| JP | 2008-507693 A | 3/2008 |
| WO | 01-090741 A2 | 11/2001 |
| WO | 2006-019487 A2 | 2/2006 |
| WO | 2011-028338 A2 | 3/2011 |

OTHER PUBLICATIONS

EESR dated Jan. 26, 2016 issued for European Patent Application No. 13 797 667.6, 8 pgs.
Office Action dated Jan. 24, 2017 issued in corresponding Japanese Patent Application No. 2014-518336, 4 pages.
Notification of Reexamination dated Oct. 9, 2018 issued for Chinese Patent Application No. 20138002860.X, 16 pgs.
Li Xinghu, Automotive Environmental Pollution and Control. National Defense Industry Press, Apr. 2011, 1st edition, Figures 3-25, 19 pgs.
Li Qin, Measurement and Control of Exhaust Pollutants in Modern Internal Combustion Engines, Mechanical Industry Press, Dec. 1998. 1st edition, 12 pgs.

* cited by examiner

EXHAUST GAS DILUTION DEVICE

CROSS-REFERENCE TO RELATED APPLICATIONS

This application is the National Stage of International Application No. PCT/JP2013/061398, filed on Apr. 17, 2013, which claims priority to JP Patent Application No. 2012-126046, filed on Jun. 1, 2012, the disclosures of each of which are incorporated in their entirety by reference herein.

TECHNICAL FIELD

The present invention relates to an exhaust gas dilution device to be used in an exhaust gas measurement system for measuring components of exhaust gas discharged from an internal combustion engine such as an engine.

BACKGROUND ART

Among conventional exhaust gas measurement systems, as disclosed in JP-A-Hei11-326161, a system for measuring particulate matters (PM) contained in engine exhaust gas is configured so as to dilute sampled engine exhaust gas with dilution air and lead the diluted exhaust gas to a PM collecting filter to thereby collect PM. Here, a ratio ($Q2/Q1$) between an engine exhaust gas flow rate $Q1$ flowing through an exhaust pipe and a sampled engine exhaust gas flow rate $Q2$ is made constant. And a mass of the PM collected by this filter is obtained by weighing by a precision balance.

Further, among exhaust gas measurement systems, as disclosed in JP-A-Hei8-226879, a constant capacity dilution sampling device (CVS) is configured so that a whole quantity of engine exhaust gas is diluted with dilution air and controlled so as to make a total flow rate obtained by summing up them constant all the time and a part of the diluted engine exhaust gas is sampled in a bag at a constant flow rate. Here, a ratio ($Q_4/Q_3$) between a total flow rate $Q_3$ controlled by the CVS and a diluted exhaust gas $Q_4$ sampled to the bag is made constant. And the diluted engine exhaust gas in the bag is analyzed by a gas analyzer.

Further, among the exhaust gas measurement systems, as disclosed in JP-A 2008-507693, a bag mini-diluter (BMD) is configured so as to sample a part of engine exhaust gas to be diluted with dilution air so as to be a constant dilution ratio so that a part of the diluted engine exhaust gas is sampled to the bag at a flow rate proportional to the flow rate of the engine exhaust gas. Here, a ratio ($Q_5 / Q_1$) between an engine exhaust gas flow rate $Q_1$ flowing through an exhaust pipe and a diluted exhaust gas flow rate $Q_5$ sampled to the bag is made constant. And the diluted engine exhaust gas in the bag is analyzed by a gas analyzer.

However, in the case where the exhaust gas measurement system is incorporated with the plurality of measurement instruments, a dilution sampling device dedicated to each of the plurality of measurement instruments is needed, and therefore there is a problem that the exhaust gas measurement system is increased in size. Moreover, due to difference in portions for sampling engine exhaust gas and difference in diluting methods every measurement instrument, properties of exhaust gas introduced to each of the measurement instruments are to be different, and therefore there is a problem that the reliability of the comparison results is bad even though the measurement results of each of the measurement instruments are compared.

SUMMARY OF INVENTION

Technical Problem

Therefore, the present invention has been made in order to collectively solve the above problems, and an essential expected object thereof is intended that diluted exhaust gas is supplied to a plurality of measurement instruments including a PM measurement instrument and an exhaust gas measurement instrument by a single exhaust gas dilution device to thereby reduce in size an exhaust gas measurement system incorporated with the exhaust gas dilution device and to measure the exhaust gas diluted with the same exhaust gas under the same dilution condition in the plurality of measurement instruments including the PM measurement instruments and the exhaust gas measurement instruments.

Solution to Problem

That is, an exhaust gas dilution device according to the present invention includes:

a sampling port which is connected with a sampling line for sampling, as sample gas, a part of exhaust gas flowing through an exhaust pipe which is connected with an internal combustion engine;

a dilution gas supply port which is connected with a dilution gas supply line for supplying dilution gas for diluting sampled exhaust gas;

a diluter communicating with the sampling port and the dilution gas supply port to thereby dilute the sample gas with the dilution gas;

a main flow path which is connected with the diluter and through which the diluted exhaust gas diluted by the diluter flows;

a plurality of measurement instrument ports which are provided in a plurality of branching flow paths branched from the main flow path and which are connected with measurement instrument lines, each of the measurement instrument lines having any one of measurement instruments including a PM measurement instrument and an exhaust gas measurement instrument;

a plurality of branching flow rate adjustment mechanisms for adjusting a flow rate of the diluted exhaust gas flowing through each of the branching flow paths; and a control device for controlling the plurality of branching flow rate adjusting mechanisms, wherein the control device includes:

an exhaust gas flow rate acquisition part for acquiring an exhaust gas flow rate related signal that directly or indirectly indicates an exhaust gas flow rate flowing through the exhaust pipe; and a flow rate adjustment mechanism control part for controlling the plurality of branching flow rate adjusting mechanisms using, as a parameter, the exhaust gas flow rate indicated by the exhaust gas flow rate related signal acquired by the exhaust gas flow rate acquisition part and adjusting the diluted exhaust gas flow rates flowing through the plurality of measurement instrument lines.

With this configuration, by supplying the diluted exhaust gas to the plurality of measurement instruments including the PM measurement instrument and the exhaust gas measurement instrument via the branching flow paths from the main flow path through which the diluted exhaust gas diluted by the diluter flows, the diluted exhaust gas can be supplied to the plurality of measurement instruments including the PM measurement instrument and the exhaust gas measurement instrument by a single exhaust gas dilution device. At this time, by controlling the branching flow rate adjustment mechanism by the control device using the exhaust gas flow rate, as a parameter, indicated by the exhaust gas flow rate related signal flowing through the exhaust pipe, a dilution ratio or a diversion ratio of the diluted exhaust gas flowing through each of the measurement instruments can be made a desirable value. Therefore, the exhaust gas measurement system incorporated with the exhaust gas dilution device of the present invention can be reduced in size, and since it is not necessary to prepare a dilution sampling device every measurement instrument, a cost can be also reduced. Further, since the exhaust gas diluted by a single exhaust gas dilution device can be supplied to the plurality of measurement instruments including the PM measurement instrument and the exhaust gas measurement instrument, the exhaust gas diluted with the same exhaust gas under the same dilution condition can be measured, and in the case where measurement results of the plurality of measurement instruments are compared, the reliability of the comparison results thereof can be improved. In addition, since the diluted exhaust gas to be supplied to the plurality of measurement instruments including the PM measurement instrument and the exhaust gas measurement instrument is produced by a single exhaust gas dilution device, there is also an effect that it is easy to incorporate an application such as switching a sampling ON/OFF in synchronization with stopping and starting of an engine and switching a sampling ON/OFF by confirming a concentration of a prescribed component of the exhaust gas. Further, it is sufficient only to confirm an operation of a single exhaust gas dilution device, and therefore a maintenance work can be also facilitated.

In addition, in the present invention, since the exhaust gas dilution device includes the branching flow rate adjustment mechanism, the configuration of the measurement instrument lines connected to the exhaust gas dilution device can be simplified.

Further, an exhaust gas dilution device according to the present invention includes:

a sampling port which is connected with a sampling line for sampling, as sample gas, a part of exhaust gas flowing through an exhaust pipe which is connected with an internal combustion engine;

a dilution gas supply port which is connected with a dilution gas supply line for supplying dilution gas for diluting sampled exhaust gas;

a diluter communicating with the sampling port and the dilution gas supply port to thereby dilute the sample gas with the dilution gas;

a main flow path which is connected with the diluter and through which the diluted exhaust gas diluted by the diluter flows;

a plurality of measurement instrument ports which are provided in a plurality of branching flow paths branched from the main flow path and which are connected with measurement instrument lines, each of the measurement instrument lines having any one of measurement instruments including a PM measurement instrument and an exhaust gas measurement instrument and a branching flow rate adjustment mechanism; and a control device for controlling the plurality of branching flow rate adjusting mechanisms, wherein the control device includes:

an exhaust gas flow rate acquisition part for acquiring an exhaust gas flow rate related signal that directly or indirectly indicates an exhaust gas flow rate flowing through the exhaust pipe; and a flow rate adjustment mechanism control part for controlling the plurality of branching flow rate adjusting mechanisms using, as a parameter, the exhaust gas flow rate indicated by the exhaust gas flow rate related signal acquired by the exhaust gas flow rate acquisition part. and adjusting the diluted exhaust gas flow rates flowing through the plurality of measurement instrument lines.

With this configuration, by supplying the diluted exhaust gas to the plurality of measurement instruments including the PM measurement instrument and the exhaust gas measurement instrument via the branching flow paths from the main flow path through which the diluted exhaust gas diluted by the diluter flows, the diluted exhaust gas can be supplied to the plurality of measurement instruments including the PM measurement instrument and the exhaust gas measurement instrument by a single exhaust gas dilution device. At this time, by controlling the branching flow rate adjustment mechanism by the control device using the exhaust gas flow rate, as a parameter, indicated by the exhaust gas flow rate related signal flowing through the exhaust pipe, a dilution ratio or a diversion ratio of the diluted exhaust gas flowing through each of the measurement instruments can be made a desirable value. Therefore, the exhaust gas measurement system incorporated with the exhaust gas dilution device of the present invention can be reduced in size, and since it is not necessary to prepare a dilution sampling device every measurement instrument, a cost can be also reduced. Further, since the exhaust gas diluted by a single exhaust gas dilution device can be supplied to the plurality of measurement instruments including the PM measurement instrument and the exhaust gas measurement instrument, the exhaust gas diluted with the same exhaust gas under the same dilution condition can be measured, and in the case where measurement results of the plurality of measurement instruments including the PM measurement instrument and the exhaust gas measurement instrument are compared, the reliability of the comparison results thereof can be improved. In addition, since the diluted exhaust gas to be supplied to the plurality of measurement instruments including the PM measurement instrument and the exhaust gas measurement instrument is produced by a single exhaust gas dilution device, there is also an effect that it is easy to incorporate an application such as switching a sampling ON/OFF in synchronization with stopping and starting of an engine or switching a sampling ON/OFF by confirming a concentration of a prescribed component of the exhaust gas. Further, it is sufficient only to confirm an operation of a single exhaust gas dilution device, and therefore a maintenance work can be also facilitated.

In addition, in the present invention, since the measurement instrument lines including the measurement instruments and the branching flow rate adjustment mechanisms are configured so as to be connected to the exhaust gas dilution device, it is not necessary to provide a branching flow rate adjustment mechanism in the exhaust gas dilution device, and therefore the exhaust gas dilution device can be reduced in size.

It is desirable that there is further included a main flow rate adjustment mechanism provided in the main flow path to adjust the flow rate of the diluted exhaust gas flowing through the main flow path and that the flow rate adjustment mechanism control part controls the main flow rate adjustment mechanism or the plurality of branching flow rate adjustment mechanism using, as the parameter, the exhaust gas flow rate indicated by the exhaust gas flow rate related signal acquired by the exhaust gas flow rate acquisition part to thereby adjust the diluted exhaust gas flow rate flowing through the plurality of measurement instrument lines. With this configuration, the dilution ratio or the diversion ratio of the diluted exhaust gas flowing each of the measurement instruments can be made further appropriately desired value, respectively.

As a specific embodiment aspect for supplying diluted exhaust gas of a desired diversion ratio to the plurality of measurement instruments using the exhaust gas dilution device of the present invention, it is desirable that the flow rate adjustment mechanism control part controls the main flow rate adjustment mechanism to thereby make a ratio constant between the exhaust gas flow rate flowing through the exhaust pipe and the sampling flow rate flowing through the sampling line.

It is desirable that the flow rate adjustment mechanism control part controls the main flow rate adjustment mechanism to thereby make a ratio constant between the exhaust gas flow rate flowing through the exhaust pipe and the sampling flow rate flowing through the sampling line and controls the plurality of branching flow rate adjustment mechanisms to thereby make a ratio constant between the exhaust gas flow rate flowing through the exhaust pipe and the diluted exhaust gas flow rate flowing through each of the measurement instrument lines. With this configuration, the diluted exhaust gas of a desired dilution ratio and a diversion ratio can be supplied to the plurality of measurement instruments. Although a dilution ratio, a retention time and a temperature range inside the diluter are defined by a recent year exhaust gas testing restriction, since the same sampling conditions can be made irrespective of an engine size in the present method, a setting can be made in conformity with the exhaust gas testing restriction irrespective of the engine size.

Further, it is desirable that the flow rate adjustment mechanism control part controls the plurality of branching flow rate control mechanisms to thereby make a ratio constant between any two of the diluted exhaust gas flow rates flowing through the respective measurement instrument lines. With this configuration, it becomes easy to control the diversion ratio of the diluted exhaust gas flowing through the respective measurement instrument lines to be constant.

Advantageous Effects of Invention

According to the present invention configured as described above, by supplying diluted exhaust gas to a plurality of measurement instruments by a single exhaust gas dilution device, the exhaust gas measurement system incorporated with the exhaust gas dilution device can be reduced in size, and the exhaust gas diluted with the same exhaust gas under the same dilution condition can be measured in a plurality of measurement instruments.

REFERENCE SIGNS LIST

Figure 1:
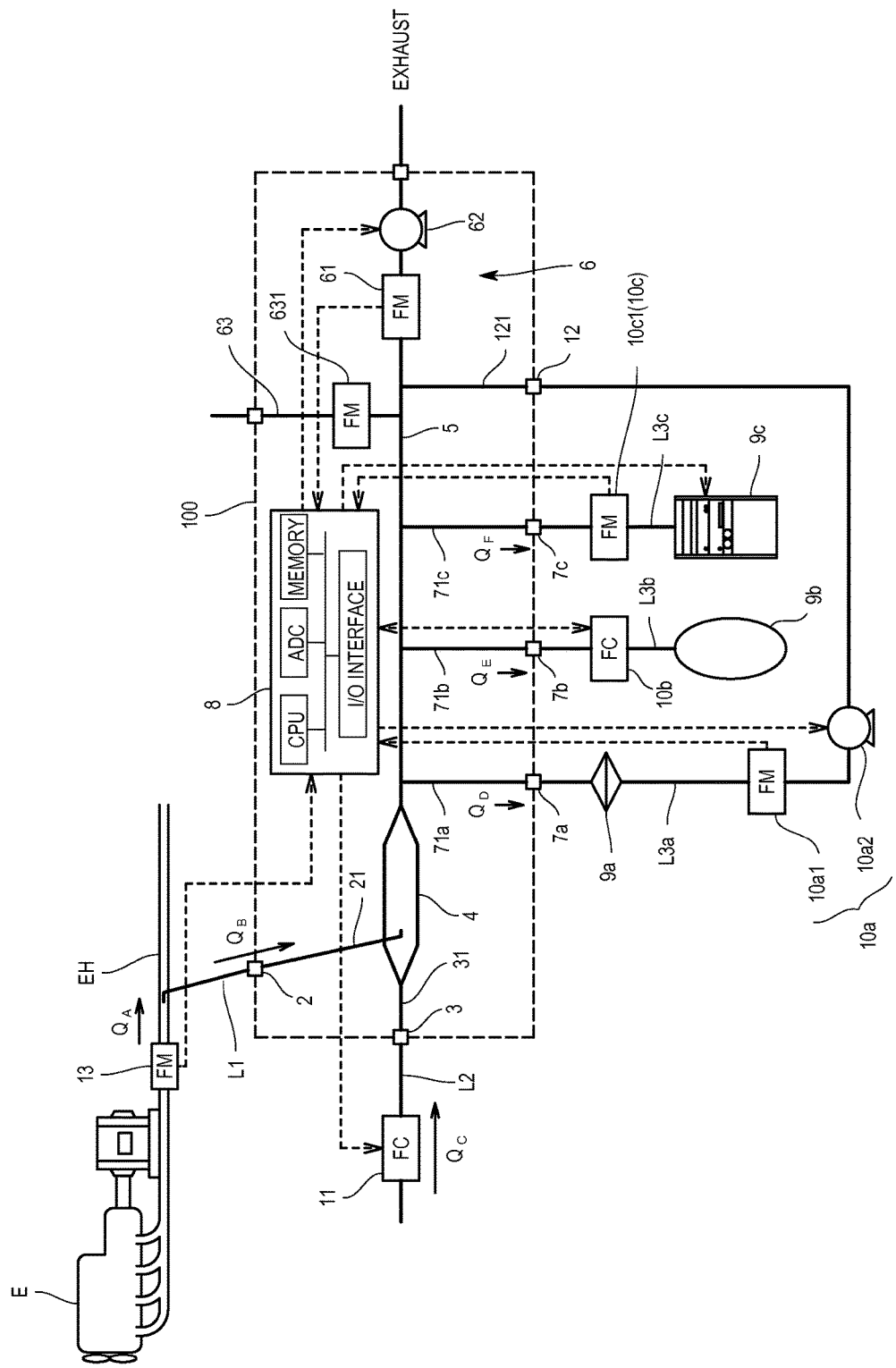
FIG. 1 is a schematic diagram of an exhaust gas measurement system using an exhaust gas dilution device of the present embodiment.

100 . . . Exhaust gas dilution device
E . . . Internal combustion engine
EH . . . Exhaust pipe
L1 . . . Sampling line
L3a to L3c . . . Measurement instrument line
L2 . . . Dilution air supply line (dilution gas supply line)
2 . . . Sampling port
3 . . . Dilution air supply port (dilution gas supply port)
4 . . . Diluter
5 . . . Main flow path
6 . . . Main flow rate adjustment mechanism
7a to 7c . . . Measurement instrument port
8 . . . Control device
81 . . . Exhaust gas flow rate acquisition part
82 . . . Flow rate adjustment mechanism control part
9a to 9c . . . Measurement instrument
10a to 10c . . . Branching flow rate adjustment mechanism

DESCRIPTION OF EMBODIMENTS

The following describes an exhaust gas dilution device 100 according to the present invention with reference to drawings.

The exhaust gas dilution device 100 according to the present embodiment is, for example, a portable one that samples a part of engine exhaust gas (simply referred to as "exhaust gas" hereinafter) flowing through an exhaust pipe EH connected to an engine E to be diluted and supplied to a plurality of measurement instruments.

Specifically, as shown in FIG. 1, this device includes: a sampling port 2 that is connected with a sampling line L1 which samples a part of exhaust gas flowing through an exhaust pipe EH as sampling gas; a dilution air supply port (dilution gas supply port) 3 that is connected with a dilution air supply line (dilution gas supply line) L2 which supplies dilution air as dilution gas for diluting the sampled exhaust gas; a single diluter 4 that communicates with the sampling port 2 and the dilution air supply port 3 to thereby dilute the sample gas with the dilution air; a main flow path 5 which is connected to the diluter 4 and through which the diluted exhaust gas diluted by the diluter 4 flows; a main flow rate adjustment mechanism 6 that is provided on the main flow path 5 to adjust a flow rate of the diluted exhaust gas flowing through the main flow path 5; a plurality of measurement instrument ports 7a to 7c that are provided in a plurality of branching flow paths 71a to 71c branched from the main flow path 5 and that are connected with measurement instrument lines L3a to L3c which respectively includes measurement instruments 9a to 9c and branching flow rate adjustment mechanisms 10a to 10c; and a control device 8 that controls the main flow rate adjustment mechanism 6 and the plurality of branching flow rate adjustment mechanisms 10a to 10c.

On the dilution air supply line L2 connected to the dilution air supply port 3, there is provided a dilution air flow rate adjustment mechanism 11 for adjusting a dilution air flow rate flowing through the dilution air supply line L2 to be supplied to the diluter 4. This dilution air flow rate adjustment mechanism 11 is configured of a massflow controller and controlled by the control device 8 to be described later.

The diluter 4 is a dilution tunnel having an upstream side connected with a first flow path 21 which has the sampling port 2 at one end and having the upstream side connected with a second flow path 31 which has the dilution air supply port 3 at one end. And the main flow path 5 is connected to a downstream side of the dilution tunnel 4.

In FIG. 1, the main flow rate adjustment mechanism 6 provided on the downstream side of the main flow path 5 is configured of a main flowmeter 61 for measuring a diluted exhaust gas flow rate flowing through the main flow path 5 and a revolution number controllable pump 62 provided on the downstream side of the main flowmeter 61. The revolution number of this pump 62 is controlled by the control device 8 to be described later. Further, this main flow rate adjustment mechanism 6 is connected with a flow rate compensation line 63 for supplying to the main flow path 5 and compensating the flow rates flowing to the second measurement instrument (exhaust gas sampling bag 9b) and the third measurement instrument (exhaust gas analyzer 9c) to be described later. This flow rate compensation line 63 is connected to the upstream side of the main flowmeter 61 and is provided with a flowmeter 631 for measuring a flow rate of compensation air flowing through the flow rate compensation line 63.

The plurality of measurement instrument ports 7a to 7c include: a first measurement instrument port 7a connected with the first measurement instrument line L3a provided with a PM collecting filter 9a which is a PM measurement instrument for collecting particulate matters (PM) contained in the diluted exhaust gas; a second measurement instrument port 7b connected with the second measurement instrument line L3b provided with an exhaust gas sampling bag 9b which is an exhaust gas measurement instrument for sampling the diluted exhaust gas; and a third measurement instrument port 7c connected with the third measurement instrument line L3c provided with an exhaust gas analyzer 9c for continuously measuring various components contained in the diluted exhaust gas.

The first measurement instrument line L3a is provided with the first branching flow rate adjustment mechanism 10a on the downstream side of the PM collecting filter 9a. The first branching flow rate adjustment mechanism 10a of the present embodiment is configured of a first flowmeter 10a1 for measuring a flow rate of the diluted exhaust gas flowing through the first measurement instrument line L3a and a revolution number controllable first pump 10a2 provided on the downstream side of the first flowmeter 10a1. The revolution number of this first pump 10a2 is controlled by the control device 8 to be described later. Thus, the flow rate of the diluted exhaust gas flowing through the first measurement instrument line L3a is adjusted. Note that a lower end portion of this first measurement instrument line L3a is connected to the main flow path 5. That is, the downstream side of the first measurement instrument line L3a is connected to a connection port 12 for connecting the downstream side of the first measurement instrument line L3a to the main flow path 5. A connection internal flow path 121 having this connection port 12 at one end is confluent with the main flow path 5 on the upstream side of the main flowmeter 61 of the main flow rate adjustment mechanism 6.

The second measurement instrument line L3b is provided with the branching flow rate adjustment mechanism 10b such as a massflow controller for adjusting a flow rate of the diluted exhaust gas flowing through the second measurement instrument line L3b, on the upstream side of the exhaust gas sampling bag 9b. This branching flow rate adjustment mechanism 10b is controlled by the control device 8 to be described later. Thus, the flow rate of the diluted exhaust gas flowing through the second measurement instrument line L3b is adjusted.

The third measurement instrument line L3c is provided with the third flowmeter 10c1 for measuring the flow rate of the diluted exhaust gas flowing through the third measurement instrument line L3c, on the upstream side of the exhaust gas analyzer 9c. And by controlling a pump (not shown) provided inside the exhaust gas analyzer 9c by the control device 8 to be described later, the flow rate of the diluted exhaust gas flowing through the third measurement instrument line L3c is adjusted. That is, the branching flow rate adjustment mechanism 10c is configured of the third flowmeter 10c1 and the pump of the exhaust gas analyzer 9c.

Figure 2:
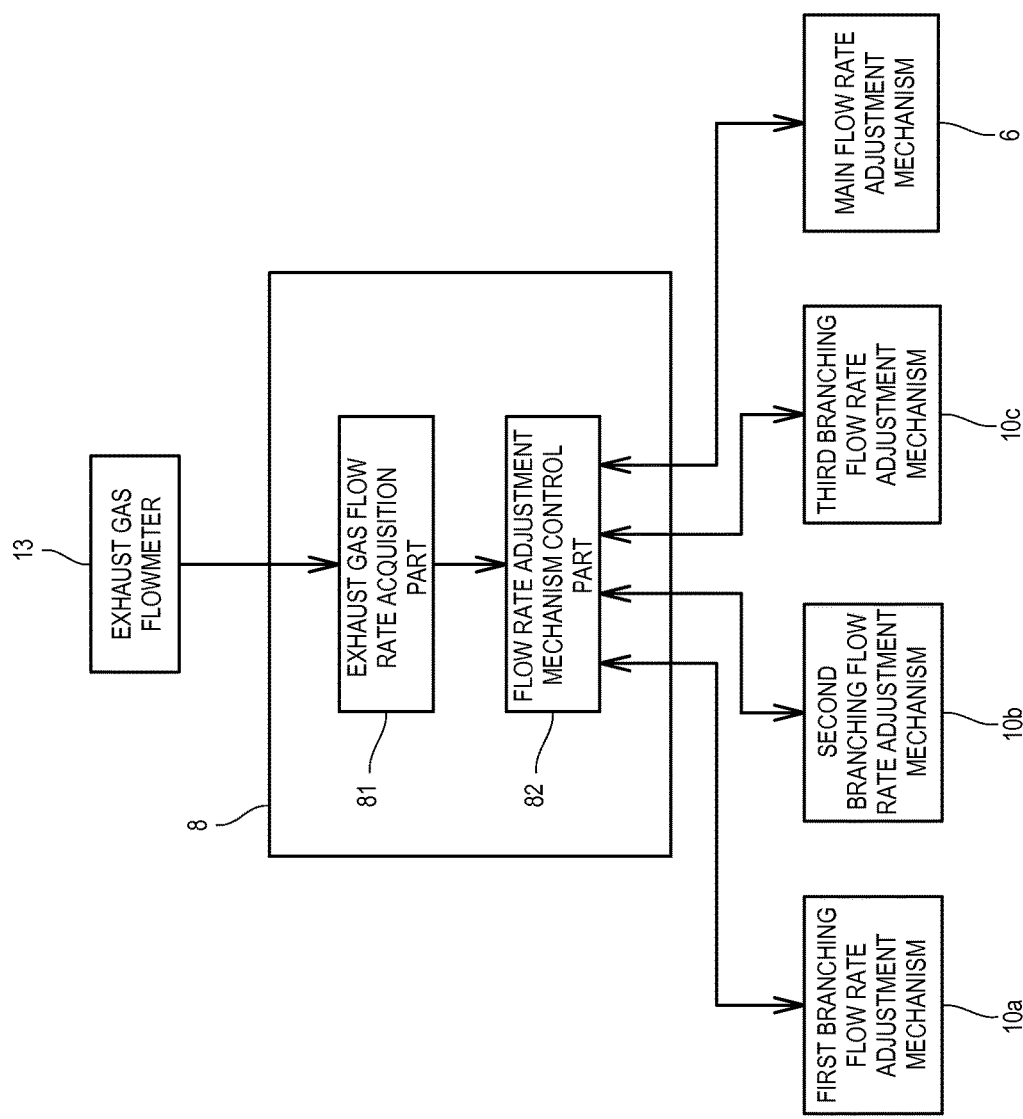
FIG. 2 is a functional configuration diagram of a control device in the same embodiment.

The control device 8 controls the main flow rate adjustment mechanism 6, the branching flow rate adjustment mechanisms 10a to 10c and a dilution air flow rate adjustment mechanism 11 based on the flow rate of the exhaust gas flowing through the exhaust pipe EH so as to be a proportional sampling by a predetermined dilution ratio and a diversion ratio. In specific, this control device 8 is a general-purpose and dedicated computer provided with a CPU, a memory, an I/O interface, an AD converter and the like, and by rendering the CPU, peripherals and the like to be in cooperation in accordance with a predetermined program stored in a predetermined area of the memory, there exhibits functions as an exhaust gas flow rate acquisition part 81, a flow rate adjustment mechanism control part 82 and the like, as shown in FIG. 2.

The exhaust gas flow rate acquisition part 81 acquires an exhaust gas flow rate related signal which is a measurement signal directly indicating an exhaust gas flow rate from an exhaust gas flowmeter 13 which is provided on the exhaust pipe EH to measure an exhaust gas flow rate $Q_A$ flowing through the exhaust pipe EH. Then, the exhaust gas flow rate acquisition part 81 outputs the exhaust gas flow rate related signal acquired from the exhaust gas flowmeter 13 to the flow rate adjustment mechanism control part 82. Note that, as the exhaust gas flowmeter 13, a thermal type flowmeter, a pitot-tube type flowmeter, a differential pressure type flowmeter, an ultrasonic type flow meter and the like are available. In addition, the exhaust gas flow rate acquisition part 81 may also acquire an exhaust gas flow rate related signal indirectly indicating an exhaust gas flow rate $Q_A$ flowing through the exhaust pipe EH. Note that, as the exhaust gas flow rate related signal indirectly indicating the exhaust gas flow rate $Q_A$, there may be considered such as an air-fuel ratio (A/F) of an engine.

The flow rate adjustment mechanism control part 82 acquires the exhaust gas flow rate related signal to calculate the exhaust gas flow rate $Q_A$ indicated by the exhaust gas flow rate related signal and controls the main flow rate adjustment mechanism 6 and the branching flow rate adjustment mechanisms 10a to 10c using the exhaust gas flow rate $Q_A$ as follows. Note that, in the present embodiment, by controlling the dilution air flow rate adjustment mechanism 11 by the control device 8, a dilution air flow rate $Q_C$ is adjusted so as to make the dilution ratio in the diluter 4 constant.

In specific, the flow rate adjustment mechanism control part 82 controls the main flow rate adjustment mechanism 6 based on the exhaust gas flow rate $Q_A$ and makes a ratio $(Q_B/Q_A)$ constant between the exhaust gas flow rate $Q_A$ flowing through the exhaust pipe EH and the sampling flow rate $Q_B$ flowing through the sampling line L1. Further, the flow rate adjustment mechanism control part 82 controls the first and second branching flow rate adjustment mechanisms 10a and 10b and makes ratios $(Q_D/Q_A, Q_E/Q_A)$ constant between the exhaust gas flow rate $Q_A$ flowing through the exhaust pipe EH and diluted exhaust gas flow rates $Q_D$ and $Q_E$ flowing through the first and second measurement instrument lines L3a and L3b. Note that the third branching flow rate adjustment mechanism 10c is controlled so that a diluted gas flow rate $Q_F$ flowing through the third measurement instrument line L3c becomes a sample gas flow rate measurable with a predetermined precision in the exhaust gas analyzer 9c.

Thus, by controlling the main flow rate adjustment mechanism 6 and the branching flow rate adjustment mechanisms 10 and 10b, the dilution ratio of the diluted exhaust gas flowing through the first to third measurement instrument lines L3a to L3c becomes ($Q_B/(Q_B+Q_C)$). Note that, the diversion ratio of the diluted exhaust gas flowing through the first measurement instrument line L3a becomes ($Q_B/Q_A \times Q_D/(Q_B+Q_C)$), the diversion ratio of the diluted exhaust gas flowing through the second measurement instrument line L3b becomes ($Q_B/Q_A \times Q_E/(Q_B+Q_C)$), and the diversion ratio of the diluted exhaust gas flowing through the third measurement instrument line L3c becomes ($Q_B/Q_A \times Q_F/(Q_B+Q_C)$). At this time, it is desirable in view of making the branch ratio constant that, by controlling the branching flow rate adjustment mechanisms 10a and 10b by the flow rate adjustment mechanism control part 82, the ratio between any two of the diluted exhaust gas flow rates flowing through the first to third measurement instrument lines L3a to L3c is made constant.

According to the exhaust gas dilution device 100 according to the present embodiment configured as described above, by supplying the diluted exhaust gas to the plurality of measurement instruments 9a to 9c including the PM measurement instrument and the exhaust gas measurement instrument from the main flow path 5 through which the diluted exhaust gas diluted by the diluter 4 flows, via the branching flow paths 71a to 71c, the diluted exhaust gas can be supplied to the plurality of measurement instruments 9a to 9c including the PM measurement instrument and the exhaust gas measurement instrument by a single exhaust gas dilution device 100. At this time, by controlling the main flow rate adjustment mechanism 6 and the branching flow rate adjustment mechanisms 10a and 10b by the control device 8, the dilution ratio and the diversion ratio of the diluted exhaust gas flowing through the respective measurement instruments 9a and 9b can be made desirable values. Therefore, the exhaust gas measurement system incorporated with the exhaust gas dilution device 100 can be reduced in size, and since it is not necessary to prepare a dilution sampling device for each of the measurement instruments 9a to 9c, the cost can be also reduced.

Further, since the exhaust gas diluted by a single exhaust gas dilution device 100 can be supplied to the plurality of measurement instruments 9a to 9c including the PM measurement instrument and the exhaust gas measurement instrument, the exhaust gas diluted with the same exhaust gas under the same dilution condition can be measured, and in the case where measurement results of the plurality of measurement instruments 9a to 9c including the PM measurement instrument and the exhaust gas measurement instrument are compared, the reliability of the comparison results thereof can be improved.

In addition, since the diluted exhaust gas to be supplied to the plurality of measurement instruments 9a to 9c including the PM measurement instrument and the exhaust gas measurement instrument is produced by a single exhaust gas dilution device 100, there is also an effect that it is easy to incorporate an application such as switching a sampling ON/OFF in synchronization with stopping and starting of an engine and switching a sampling ON/OFF by confirming a concentration of a prescribed component of the exhaust gas. Further, it is sufficient only to confirm an operation of a single exhaust gas dilution device 100, and therefore a maintenance work can be also facilitated. Further, in the present embodiment, since the measurement instrument lines L3a to L3c including the measurement instruments 9a to 9c and the branching flow rate adjustment mechanisms 10a to 10c are configured so as to be connected to the exhaust gas dilution device 100, it is not necessary to provide a branching flow rate adjustment mechanism in the exhaust gas dilution device 100, and therefore the exhaust gas dilution device 100 can be reduced in size. Further, since the exhaust gas dilution device 100 includes the sample gas port 2, the dilution air supply port 3, the plurality of measurement instrument ports 7a to 7c and the like, each line may be only connected after setting in a predetermined place, it can be appropriately used as a portable one. In addition, although a dilution ratio, a retention time and a temperature range inside the diluter 4 are defined by a recent exhaust gas testing restriction, since the same sampling conditions can be made irrespective of an engine size in the present method, a setting can be made in conformity with the exhaust gas testing restriction irrespective of the engine size.

Note that the present invention should not be limited to the above embodiment.

For example, the flow rate adjustment mechanism control part 82 of the embodiment may be configured so as to control the main flow rate adjustment mechanism 6 and the branching flow rate adjustment mechanisms 10a and 10b as follows. That is, the flow rate adjustment mechanism control part 82 controls the main flow rate adjustment mechanism 6 and makes a ratio ($Q_B/Q_A$) constant between the exhaust gas flow rate $Q_A$ flowing through the exhaust pipe EH and the sampling flow rate $Q_B$ flowing through the sampling line L1. Further, the flow rate adjustment mechanism control part 82 may control the first and second branching flow rate adjustment mechanisms 10a and 10b and make the diluted exhaust gas flow rates $Q_D$ and $Q_E$ flowing through the first and second measurement instrument lines L3a and L3b constant.

Also, the flow rate adjustment mechanism control part 82 may control the main flow rate adjustment mechanism 6 to make the sampling flow rate $Q_B$ flowing through the sampling line L1 constant, and control the first and second branching flow rate adjustment mechanisms 10a and 10b and make ratios ($Q_D/Q_A$, $Q_E/Q_A$) constant between the exhaust gas flow rate $Q_A$ flowing through the exhaust pipe EH and diluted exhaust gas flow rates $Q_D$ and $Q_E$ flowing through the first and second measurement instrument lines L3a and L3b.

Further, in view of making only the branch ratio constant, it is sufficient that the flow rate adjustment mechanism control part 82 controls the main flow rate adjustment mechanism 6 and makes a ratio ($Q_B/Q_A$) constant between the exhaust gas flow rate $Q_A$ flowing through the exhaust pipe EH and the sampling flow rate $Q_B$ flowing through the sampling line L1.

Further, the dilution air flow rate flowing through the dilution air supply line L2 may be adjusted to be a constant flow rate by the dilution air flow rate adjustment mechanism 11.

Figure 3:
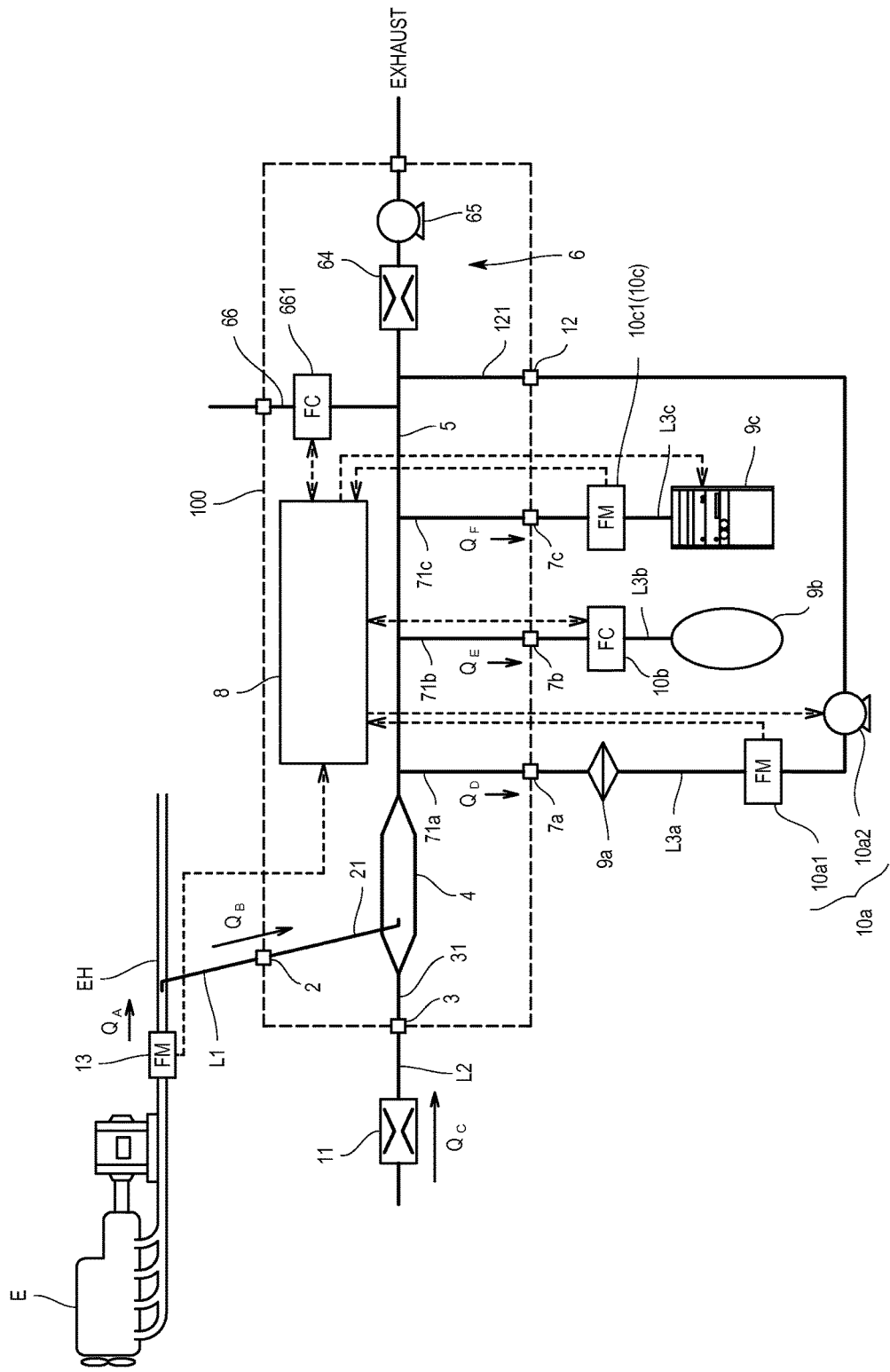
FIG. 3 is a schematic diagram of an exhaust gas measurement system using an exhaust gas dilution device of a modified embodiment.

Further, although the main flow rate adjustment mechanism 6 of the above embodiment includes the main flowmeter 61, a variable capacity type pump 62 and the flow rate compensation line 63 including a flowmeter 631, it may include a constant flow rate regulator 64 such as a critical flow rate venture (CFV), a constant capacity pump 65 and a flow rate compensation line 66 including a flow rate adjustment mechanism 661, as shown in FIG. 3. Further, the dilution air flow rate adjustment mechanism 11 provided on the dilution air supply line L2 may be a constant flow rate regulator such as a critical flow rate venture (CFV).

Figure 4:
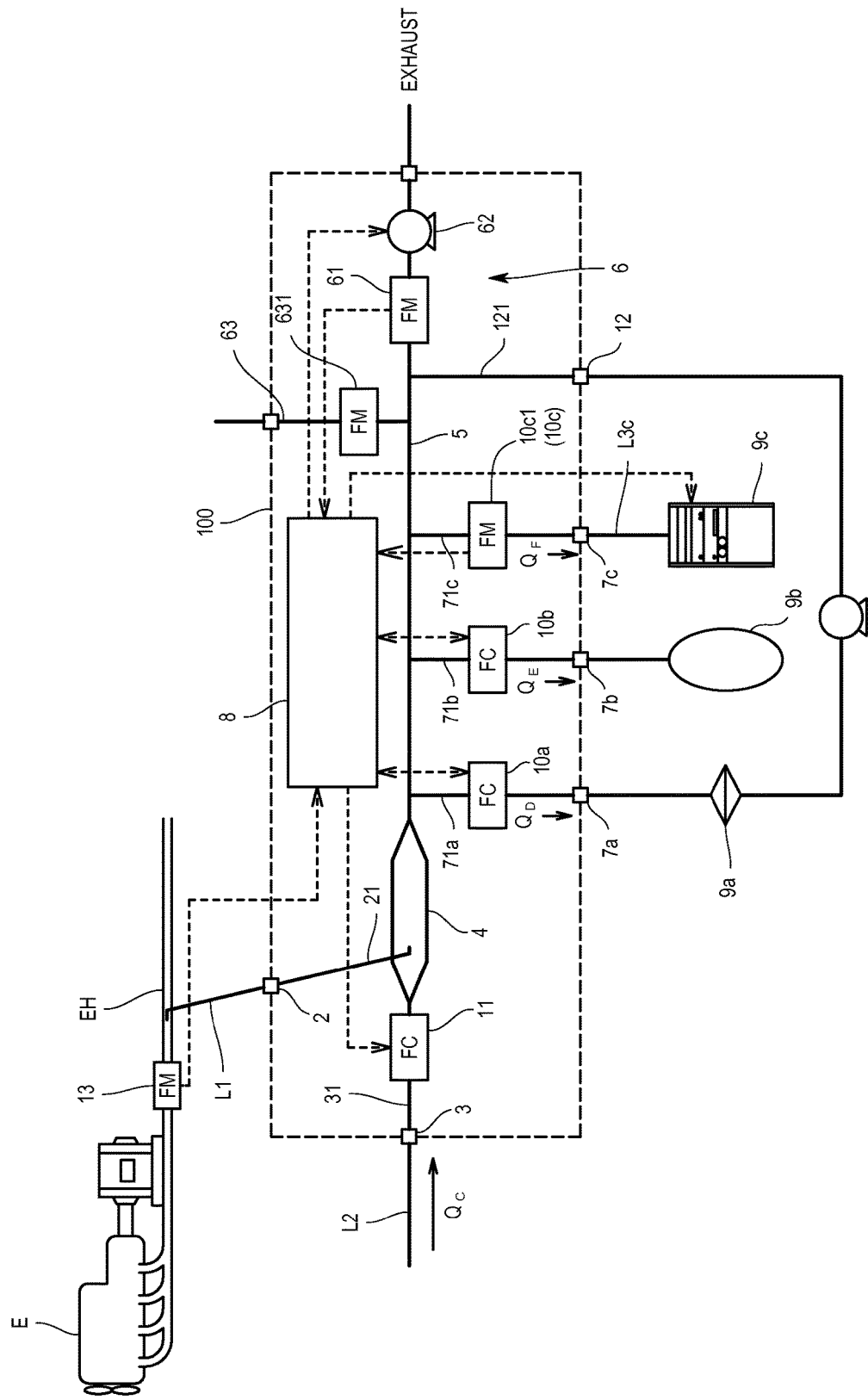
FIG. 4 is a schematic diagram of an exhaust gas measurement system using an exhaust gas dilution device of a modified embodiment.

Further, in the embodiment, although the first, second and third branching flow rate adjustment mechanisms 10a to 10c provided on the first, second and third measurement instrument lines L3a to L3c are provided outside the exhaust gas dilution device 100, the first, second and third branching flow rate adjustment mechanisms 10a to 10c may be provided on respective branching flow paths 71a to 71c inside the device 100, as shown in FIG. 4. Similarly, as shown in FIG. 4, the dilution air flow rate adjustment mechanism 11 provided on the dilution air supply line L2 may be provided on a second flow path 31 between the dilution air supply port 3 and the diluter 4.

In addition, the first, second and third measurement instrument lines L3a to L3c should not be limited to three as in the embodiment, and these lines may be three or more. Further, as a kind of the measurement instruments 9a to 9c, it may only be a measurement instrument measurable using diluted exhaust gas, and it may be, for example, a solid particle number measurement device (SPCS) using a laser scattering condensed particle counter (CPC), a gas absorption bottle (impinge), and the like.

In addition, it is needless to say that the present invention should not be limited to the above embodiments and various modifications thereof can be made in a range without departing from the spirit thereof.

INDUSTRIAL APPLICABILITY

According to the exhaust gas dilution device of the present invention, by supplying diluted exhaust gas to a plurality of measurement instruments by a single exhaust gas dilution device, the exhaust gas measurement system incorporated with the exhaust gas dilution device can be reduced in size, and the exhaust gas diluted with the same exhaust gas under the same dilution condition can be measured in a plurality of measurement instruments.

The invention claimed is:
1. An exhaust gas dilution device comprising:
a sampling port which is connected with a sampling line for sampling, as sample gas, a part of exhaust gas flowing through an exhaust pipe which is connected with an internal combustion engine;
a dilution gas supply port which is connected with a dilution gas supply line for supplying dilution gas for diluting sampled exhaust gas;
a diluter communicating with the sampling port and the dilution gas supply port to dilute the sample gas with the dilution gas;
a main flow path which is connected with the diluter and through which diluted exhaust gas diluted by the diluter flows;
a plurality of measurement instrument ports which are provided in a plurality of branching flow paths branched from the main flow path and which are connected with measurement instrument lines, each of the measurement instrument lines having any one of measurement instruments including a PM measurement instrument and an exhaust gas measurement instrument;
a main flow rate adjustment mechanism provided in the main flow path to adjust a flow rate of the diluted exhaust gas flowing through the main flow path;
a plurality of branching flow rate adjustment mechanisms for adjusting a flow rate of the diluted exhaust gas flowing through each of the branching flow paths; and
a control device for controlling the plurality of branching flow rate adjustment mechanisms, wherein the control device includes
an exhaust gas flow rate acquisition part for acquiring an exhaust gas flow rate related signal that indicates a flow rate of the exhaust gas flowing through the exhaust pipe, and
a flow rate adjustment mechanism control part for controlling the plurality of branching flow rate adjustment mechanisms using, as a parameter, the flow rate of the exhaust gas and for adjusting flow rates of the diluted exhaust gas flowing through the measurement instrument lines, the flow rate adjustment mechanism control part controlling the plurality of branching flow rate adjustment mechanisms to make a ratio constant between the flow rate of the exhaust gas and each of the flow rates of the diluted exhaust gas.

2. The exhaust gas dilution device according to claim 1, wherein the flow rate adjustment mechanism control part controls the plurality of branching flow rate adjustment mechanisms to make a ratio constant between any two of the flow rates of the diluted exhaust gas.

3. The exhaust gas dilution device according to claim 1, wherein the flow rate adjustment mechanism control part controls the main flow rate adjustment mechanism using, as the parameter, the flow rate of the exhaust gas to adjust the flow rates of the diluted exhaust gas.

4. The exhaust gas dilution device according to claim 3, wherein the flow rate adjustment mechanism control part controls the main flow rate adjustment mechanism to make a ratio constant between the flow rate of the exhaust gas and the flow rate of the sample gas.

5. An exhaust gas dilution device comprising:
a sampling port which is connected with a sampling line for sampling, as sample gas, a part of exhaust gas flowing through an exhaust pipe which is connected with an internal combustion engine;
a dilution gas supply port which is connected with a dilution gas supply line for supplying dilution gas for diluting sampled exhaust gas;
a diluter communicating with the sampling port and the dilution gas supply port to dilute the sample gas with the dilution gas;
a main flow path which is connected with the diluter and through which diluted exhaust gas diluted by the diluter flows;
a main flow rate adjustment mechanism provided in the main flow path to adjust a flow rate of the diluted exhaust gas flowing through the main flow path;
a plurality of measurement instrument ports which are provided in a plurality of branching flow paths branched from the main flow path and which are connected with measurement instrument lines, each of the measurement instrument lines having any one of measurement instruments including a PM measurement instrument, an exhaust gas measurement instrument, and a branching flow rate adjustment mechanism; and
a control device for controlling the branching flow rate adjustment mechanisms, the control device including
an exhaust gas flow rate acquisition part for acquiring an exhaust gas flow rate related signal that indicates a flow rate of exhaust gas flowing through the exhaust pipe, and a flow rate adjustment mechanism control part for controlling the branching flow rate adjustment mechanisms using, as a parameter, the flow rate of the exhaust gas and for adjusting flow rates of the diluted exhaust gas flowing through the measurement instrument lines, the flow rate adjustment mechanism control part controlling the main flow rate adjustment mechanism to make a ratio between the flow rate of the exhaust gas and a flow rate of the sample gas flowing through the sampling line constant, and controlling the branching flow rate adjustment mechanisms to make a ratio constant between the flow rate of the exhaust gas and the flow rates of the diluted exhaust gas.

6. The exhaust gas dilution device according to claim 5, wherein the flow rate adjustment mechanism control part controls the branching flow rate adjustment mechanisms to make a ratio constant between any two of the flow rates of the diluted exhaust gas.

7. A method for operating an exhaust gas dilution device that includes a sampling port which is connected with a sampling line for sampling, as sample gas, a part of exhaust gas flowing through an exhaust pipe which is connected with an internal combustion engine, a dilution gas supply port which is connected with a dilution gas supply line for supplying dilution gas for diluting sampled exhaust gas, a diluter communicating with the sampling port and the dilution gas supply port to dilute the sample gas with the dilution gas, a main flow path which is connected with the diluter and through which diluted exhaust gas diluted by the diluter flows, a plurality of measurement instrument ports which are provided in a plurality of branching flow paths branched from the main flow path and which are connected with measurement instrument lines, each of the measurement instrument lines having any one of measurement instruments including a PM measurement instrument and an exhaust gas measurement instrument, a main flow rate adjustment mechanism provided in the main flow path to adjust a flow rate of the diluted exhaust gas flowing through the main flow path, a plurality of branching flow rate adjustment mechanisms for adjusting a flow rate of the diluted exhaust gas flowing through each of the branching flow paths, and a control device for controlling the plurality of branching flow rate adjustment mechanisms, the method comprising:

by the control device,
acquiring an exhaust gas flow rate related signal that indicates a flow rate of the exhaust gas flowing through the exhaust pipe,
controlling the plurality of branching flow rate adjustment mechanisms using, as a parameter, the flow rate of the exhaust gas to make a ratio constant between the flow rate of the exhaust gas and each of the flow rates of the diluted exhaust gas, and
adjusting the flow rates of the diluted exhaust gas.

* * * * *